(12) United States Patent
Hassan et al.

(10) Patent No.: US 7,378,043 B2
(45) Date of Patent: May 27, 2008

(54) LATEX GLOVES AND ARTICLES WITH GEOMETRICALLY DEFINED SURFACE TEXTURE PROVIDING ENHANCED GRIP AND METHOD FOR IN-LINE PROCESSING THEREOF

(75) Inventors: Noorman Abu Hassan, Shah Alam (MY); David M. Lucas, Petaling Jaya (MY); Fazli Shani, Puchong (MY); Dave Narasimhan, Flemington, NJ (US)

(73) Assignee: Ansell Healthcare Products LLC, Red Bank, NJ (US)

( * ) Notice: Subject to any disclaimer, the term of this patent is extended or adjusted under 35 U.S.C. 154(b) by 256 days.

(21) Appl. No.: 11/035,366

(22) Filed: Jan. 12, 2005

(65) Prior Publication Data
US 2006/0150300 A1    Jul. 13, 2006

(51) Int. Cl.
*B28B 1/38* (2006.01)
(52) U.S. Cl. .......................................... 264/28; 264/306
(58) Field of Classification Search ...................... None
See application file for complete search history.

(56) References Cited

U.S. PATENT DOCUMENTS

| | | | |
|---|---|---|---|
| 2,293,928 A | 8/1942 | Beal | |
| 2,324,735 A | 7/1943 | Spanel | |
| 2,353,877 A | 7/1944 | Chollar | |
| 2,393,298 A | 1/1946 | De Laney et al. | |
| 2,503,139 A | 4/1950 | Fabregues-Boixar | |
| 2,997,746 A | 8/1961 | O'Brien et al. | |
| 3,869,726 A | 3/1975 | Bell | |
| 3,934,062 A | 1/1976 | Tillotson et al. | |
| 4,082,862 A * | 4/1978 | Esemplare et al. | 427/133 |
| 4,143,109 A | 3/1979 | Stockum | |
| 4,218,779 A | 8/1980 | Hart et al. | |
| 4,283,244 A * | 8/1981 | Hashmi | 156/242 |
| 4,284,275 A | 8/1981 | Fletcher | |

(Continued)

FOREIGN PATENT DOCUMENTS

EP    824896 A    2/1998

(Continued)

OTHER PUBLICATIONS

Written Opinion of the International Searching Authority, Jan. 17, 2006, International Search Report, Jan. 17, 2006.

*Primary Examiner*—Mary Lynn Theisen
(74) *Attorney, Agent, or Firm*—Diehl Servilla LLC; Karen M. Whitney

(57) ABSTRACT

Latex articles with geometrically defined surface structure providing enhanced grip characteristics in dry, wet or oily environment; and a method of making same comprising applying a polymeric coagulant coating to a smooth former surface, wherein the coating becomes tacky during drying, applying discrete coagulant particles of selected size, shape and distribution to the tacky coating to attach and protrude from the former surface with the polymeric coagulant coating, dipping the former into an aqueous latex emulsion, wherein the polymeric coagulant coating and the discrete coagulating particles destabilize the latex, thereby developing a latex layer, vulcanizing and stripping the latex article inside out, and dissolving the discrete coagulant particles in water or suitable solvents to reveal the geometrically designed texture with pre-selected size, shape and distribution of impressions providing improved dry, wet and oily surface grip by removal of a fluid boundary layer.

23 Claims, 6 Drawing Sheets

U.S. PATENT DOCUMENTS

| | | |
|---|---|---|
| 4,329,312 A | 5/1982 | Ganz |
| 4,463,156 A | 7/1984 | McGary et al. |
| 4,497,072 A | 2/1985 | Watanabe |
| 4,519,098 A | 5/1985 | Dunmire et al. |
| 4,536,890 A | 8/1985 | Barnett et al. |
| 4,555,813 A | 12/1985 | Johnson |
| 4,589,940 A | 5/1986 | Johnson |
| 5,070,540 A | 12/1991 | Bettcher et al. |
| 5,284,607 A * | 2/1994 | Chen ..................... 264/37.18 |
| 5,304,337 A | 4/1994 | Chen et al. |
| 5,438,709 A | 8/1995 | Green et al. |
| 5,500,469 A * | 3/1996 | Johnsen et al. ............. 524/157 |
| 5,712,346 A * | 1/1998 | Lee ............................ 525/288 |
| 5,822,791 A | 10/1998 | Baris |
| 5,977,223 A * | 11/1999 | Ryan et al. .................. 524/221 |
| 5,993,923 A | 11/1999 | Lee |
| 6,019,922 A * | 2/2000 | Hassan et al. .............. 264/130 |
| 6,075,081 A * | 6/2000 | Nile et al. ................... 524/429 |
| 6,081,928 A | 7/2000 | Bourne |
| 6,306,514 B1 * | 10/2001 | Weikel et al. .............. 428/451 |
| 6,347,409 B1 * | 2/2002 | Nile et al. ...................... 2/168 |
| 6,378,137 B1 * | 4/2002 | Hassan et al. ............... 2/161.7 |
| 6,391,409 B1 | 5/2002 | Yeh et al. |
| 7,037,579 B2 * | 5/2006 | Hassan et al. ........... 428/295.1 |
| 2001/0011387 A1 * | 8/2001 | Yamashita et al. ............. 2/167 |
| 2001/0053421 A1 * | 12/2001 | Schaller ...................... 427/557 |
| 2002/0035744 A1 | 3/2002 | Kolcio et al. |
| 2003/0033660 A1 | 2/2003 | Sajovic |
| 2003/0037364 A1 | 2/2003 | Albert |
| 2003/0221239 A1 * | 12/2003 | Modha et al. ................ 2/161.7 |
| 2004/0122382 A1 * | 6/2004 | Johnson et al. ............. 604/292 |
| 2005/0015888 A1 * | 1/2005 | Altmann et al. ........... 8/115.51 |
| 2006/0008631 A1 * | 1/2006 | Takeyama et al. ....... 428/295.1 |
| 2006/0068140 A1 * | 3/2006 | Flather et al. ............. 428/36.1 |
| 2006/0143767 A1 * | 7/2006 | Yang et al. ...................... 2/16 |

FOREIGN PATENT DOCUMENTS

| | | |
|---|---|---|
| FR | 2448307 A1 | 9/1980 |
| GB | 418240 A | 10/1934 |
| JP | 01-258917 | 10/1989 |
| JP | 01-258917 A | 10/1989 |
| JP | 01258917 A1 | 10/1989 |
| WO | WO 00/19847 A1 | 4/2000 |
| WO | WO 02/052965 A1 | 7/2002 |
| WO | WO 03/102058 A1 | 12/2003 |
| WO | WO 2005/002375 A1 | 1/2005 |

* cited by examiner

LATEX GLOVES AND ARTICLES WITH GEOMETRICALLY DEFINED SURFACE TEXTURE PROVIDING ENHANCED GRIP AND METHOD FOR IN-LINE PROCESSING THEREOF

FIELD OF THE INVENTION

The invention relates to synthetic or natural latex gloves and articles having enhanced gripping characteristics provided by virtue of a roughened, geometrically defined, surface integrally formed on the outer surface of the glove during its in-line manufacturing process.

BACKGROUND OF THE INVENTION

Synthetic or natural latex gloves providing enhanced gripping characteristics are known to be extremely desirable, since they provide slip-resisting, gripping action, even when wet articles are handled. The external surface of the glove can be textured in order to obtain superior gripping properties. Traditional approaches include the use of textured formers, which are dipped into an aqueous latex emulsion resulting in a textured glove surface at the textured former contact surface. When the glove is inverted, the external glove surface becomes textured with a pattern representative of that on the former. Generally, the former external surface can be textured or indented in each of the finger, thumb tips, and body portions so that gloves with texture in these regions can be produced. The details of the texture produced can vary according to the requirements of the glove manufacturer. Unfortunately, this simple approach has limited applications, since dipping defects occur at the edges defining the texture, resulting in a latex film, which has holes or which tears easily at these defective regions. The textured former surface also readily degrades, and latex articles are difficult to strip from the former after cross-linking of the latex film, due to the texture present at the former-latex interface. The stripping action can tear formed latex articles or, in the worst case, produce pinholes and other defects, which may be difficult to observe but nevertheless deteriorate the overall quality and reliability of the latex product. For example, U.S. Pat. No. 6,081,928 and Int'l Pat. App. Pub. No. WO 00/19847 to Bourne disclose an elastomeric glove with enhanced grip strength. The gripping surfaces of the glove, preferably each of the finger and thumb tips and the body portions are molded with a plurality of concave indentations between 0.004 and 0.020 inches or with a plurality of suction cups with a circular border diameter ranging from 0.008 to 0.5 inches. The manufacturing process employs glove-dipping formers having surfaces comprised of a plurality of convex protrusions or suction cup structures. In another example, U.S. Pat. No. 6,254,947 to Schaller discloses flexible plastic articles bearing polymeric slip coatings and having raised/recessed roughness on their surfaces. This slip coating is comprised of a polymeric material and, at least in sections, has repeating shape deviations of the surface that are recessed in relation to a raised, net-like structure. The slip coating is applied to the interior surface of the glove—not the exterior surface of the glove—and provides slipperiness, not roughness with improved grip, since the soft slip coating material comprises polyacrylates and/or polymethacrylates and/or polysiloxanes over natural rubber. The glove is made by dipping a porcelain former with a series of indentations, and the contacted surface becomes the external surface having protrusions, while the non-contact surface with recesses becomes the skin-contact surface and receives the soft polymeric coating. In a third example, U.S. Pat. No. 5,098,755 to Tanquary et al. discloses textured thermoplastic elastomeric film, articles comprising the same, and a method of making such a film and articles. Textured and embossed films for condom articles are provided with an embossed pattern with 1,000 to 100,000 embossments per square inch of embossed surface. Dipping a latex article does not form this texture, but the embossed pattern is formed by elevated heat and/or pressure-forming conditions. Heating of latex to produce an embossed pattern generally degrades its mechanical and barrier properties.

Another approach is to produce a rough gripping surface of a glove by foaming the latex external surface. Incorporating air into the aqueous latex produces this foamed surface. Air bubbles in latex generally are spherical in shape with non-uniform bubble sizes, due to the inherent instability resulting from larger bubbles growing when they contact smaller bubbles. When air bubbles touch each other, they form a much larger foam cell, and the roughness produced is not well-controlled. For example, U.S. Pat. No. 2,393,298 to De Laney discloses rubber glove and like articles. The former is dipped first in an aqueous latex emulsion, followed by a coagulant dip to harden the first latex layer, and then dipped in a foamed second latex layer, which is dipped in aerated runny latex, and the air bubbles burst to form a porous second layer. The former is then dipped in a coagulant layer to harden and stabilize the second foamed latex layer. In a second example, U.S. Pat. No. 4,589,940 to Johnson discloses a method of making foamed, slip-resistant surfaces. The surface of the gloves provides a porous, foam surface, so that the gloves are breathable and have moisture-absorbing properties. The porous latex foam is applied to a woven or non-woven substrate. Since the substrate is porous and the foamed latex is porous (40-95% porosity), the glove thus formed is breathable. The foam is stated to be abrasion-resistant and to provide improved gripping action. In a third example, U.S. Pat. No. 4,497,072 to Watanabe discloses a porous, coated glove. The porous glove is made of a fabric material with a coating layer that has sharp projections in the shape of broken bubbles, thereby providing tenacious gripping properties. The fabric glove base is formed from knitted fabrics, woven fabrics, or staple fiber materials. The fabric is then coated with a latex foaming solution, which is solvent-based. The process of evaporation of the solvent is assisted by reduced pressure, which breaks the air bubbles, forming sharp edges. Multiple bubbles can collapse together, as shown in FIGS. 3 and 4, resulting in uncontrolled texture of the glove surface. In a fourth example, U.S. Pat. No. 6,527,990 to Yamashita et al. discloses a method for producing a rubber glove. A rubber glove is produced by sequentially immersing a glove mold, first in a coagulating, synthetic rubber latex containing thermally expansible microcapsules and blowing agents. Next, it is immersed in a rubber-incorporating latex to form a gelled rubber layer forming a rubber laminate. The rubber laminate is then heated to vulcanize the rubber laminate, and to expand the microcapsules and blowing agents creating a foam. The laminate is turned inside out with the expanded microcapsule side forming the outer surface of the glove. This method produces a rubber glove, which is excellent in anti-blocking properties (no stickiness between two contacting gloves) and grip under dry or wet conditions, by a simple procedure and for a low cost.

Another approach for texturing latex gloves is to incorporate water-soluble particles in an uncured latex layer. For example, Japanese patent JP1258917 to Kishi discloses an uneven surface skin, for example, rubber glove obtained by adhering solid granular material on unsolidified resin emulsion latex and solidifying. A latex composition coating is formed on the surface of a mold. Under the state that the latex coating is still unsolidified, particulates, which do not dissolve in latex and which dissolve in water solution, such as salt, are scattered and adhered onto the latex coating. After the coating is vulcanized, the salt is removed by being washed with water in order to obtain rubber gloves made of non-air-permeable and non-water-permeable rubber skin with fine recessed or projecting parts on their surfaces. Since the latex is still fluid prior to vulcanization, the incorporated particles are covered by latex and are not easily dissolved to produce the desired surface structure. In a second example, U.S. Pat. No. 2,997,746 to O'Brien et al. discloses a method of making a roughened rubber product. The process uses insoluble hydrophilic solids in a non-aqueous medium, such as naphtha and other hydrocarbon solvents that essentially dissolve rubber. This rubber cement has added hydrophilic solids, such as sugar or salt, and, therefore, forms a latex coating with embedded hydrophilic solids on the former, when dipped, and the hydrophilic solids are dissolved in soapy water creating a roughened surface. Note that the hydrophilic solid employed is insoluble in naphtha or other hydrocarbon solvents employed to dissolve rubber. Sugar has a specific gravity of approximately 1.4, and salt has a specific gravity of 2.165. The latex solvent solution has a specific gravity of less than 1, depending upon the choice of solvents. The hydrophilic solids are not easily suspended in the latex solvent solution, due to the settling behavior of hydrophilic solids, especially when the solid size is large. Vigorous agitation is needed to suspend the hydrophilic solids in the latex solvent solution. When a form is dipped in this latex solvent solution, it may not receive uniform distribution of hydrophilic solids due to this settling behavior, and high levels of agitation in the latex solvent solution tend to knock away any particles that are incorporated. Further, the particle is not held in place until the solvent is dried, and only a few rapidly moving particles will be captured in the latex layer formed on the former, thus producing a sparsely textured, dipped article with poor texture uniformity. The swelling of the hydrophilic solids results in voids that are much larger than the solids added to the latex cement solution and may be even larger due to solvent evaporation, resulting in voids that are essentially devoid of any shape. These voids may also combine or coalesce to form even larger voids that are much larger than the starting sugar crystals. O'Brien does not disclose nitrile rubber compositions, since solvents for nitrile rubber are not readily available.

Several other disclosures related to grip-enhancing gloves are described in U.S. Pat. No. 6,675,392 to Albert and U.S. Pat. Nos. 6,745,403 and 6,526,593 to Sajovic. They relate to a method of obtaining grip for sporting gloves by installing plastic suction cup-shaped devices onto the gloves. These features are attached later to the glove surface, are not an integral part of the glove, and provide grip in limited areas of the glove appropriate for the sporting purpose intended. These suction cups do not provide overall gripping.

There remains a need in the art for latex articles and glove surfaces that are textured and provide superior gripping properties when handling dry, wet or oily objects. The external surface of the glove must have an engineered surface, preferably with a well-designed, reproducible texture of geometrical features that assist in eliminating the fluid boundary layer between the glove's external surface and that of the object being gripped. There remains a need for a reliable process for the creation of this engineered, external textured glove surface that requires complete control of the size, the shape and the distribution of the surface features of a latex glove formed by the most commonly used industrial process of latex in-line dip processing. It is an object of the present invention to provide such latex articles and glove surfaces, as well as a process for making the same. These and other objects and advantages, as well as additional inventive features, will become apparent from the detailed description provided herein.

SUMMARY OF THE INVENTION

The present invention provides latex gloves and articles with geometrically defined surface textures that result in enhanced grip properties. The geometrical surface texture on the glove is created reproducibly according to design specifications and requirements. The design specifications include the size and shape of texture, together with the distribution of the texture across the surface of the glove. More specifically, the texture at the thumb, finger and palm regions can be individually tailored and be made different to control the gripping character of the glove.

The present invention discloses a process that precisely places the desired surface texture on the glove surface in an industrial setting in a reliable and reproducible manner. A smooth surface former having the required shape of the glove is chosen. The former is made from well-known materials commonly employed in the industry including ceramics, metals or polymers. The former is dip-coated first with a water-based, polymeric, coagulant coating having a thickness in the range of about 5 to 50 µ. The polymeric coagulant former coating composition comprises a coagulant, which can destabilize and coagulate an aqueous latex emulsion. The coagulant incorporated in the polymeric former coating is typically calcium nitrate, calcium chloride, sodium chloride, potassium chloride, aluminum chloride, aluminum sulfate; etc. These coagulants are highly soluble in water. As the water in the polymeric coagulant coating evaporates or dries, the polymeric coagulant coating become tacky. At this stage, the discrete coagulant particles of a size and shape representing the impressions required on the glove surface are chosen and are placed on the tacky polymeric coagulant coating by one or more processes. These processes can use water-soluble, partially water soluble, or totally water insoluble discrete coagulant particles, and their removal in the final step of the process will require the use of water or appropriate solvents. In its simplest form, the water-soluble, discrete coagulant particles are applied by a spray process. The spray process covers uniformly the surface of the polymeric coagulant former coating, and the water-soluble discrete coagulant particles are embedded within the coating. Other suitable processes include, but are not limited to, a fluidized bed of discrete coagulant particles contacting the tacky former coating or discrete coagulant particles carried on a flexible mesh that contacts and rolls over the tacky former surface, arranging the discrete coagulant particles in a desired pattern. Another embodiment places discrete coagulant particles of differing size, shape, and distribution in the thumb region, the palm region, and the tips of one or more fingers off the glove former. When the polymeric coagulant coating completely dries, the particles are held in place by the polymeric coagulant coating, with the discrete coagulant particles clearly protruding from the former surface. The formers with this polymeric coagulant coating with embedded discrete coagulant particles can be prepared separately and stored or produced in an in-line manufacturing process.

Generally stated, the key requirements are that the polymeric coating composition possesses adequate former surface-wetting properties and sufficient viscosity or rheology characteristics so as to form a thin layer of uniform polymeric coating. This is accomplished by adding wetting agents and viscosity modifiers to the polymeric coating composition. The coating must dry at a reasonable rate, providing a well-defined operating time period, during which the polymeric coagulant coating remains tacky to accept the application of discrete coagulant particles defining the size, shape and distribution of the desired geometrical texture of the glove surface. A typical polymeric coagulant coating composition includes polymers selected from poly N-vinyl-2-pyrrolidone (PVP), polyvinyl alcohol (PVA), polyacrylic acids (PAA), polyacrylamide (PAC), and/or a copolymer or derivative of PVP, PVA, PAA or PAC. The amount of polymer present is in the range of about 0.1 to 10 dry wt %, preferably in the range of about 0.5 to 1.5 dry wt %. The coagulant used in the polymeric former coating is selected from calcium nitrate and calcium chloride. Addition of polyglycol, which includes polyethylene glycol or polyethylene oxide/polypropylene oxide copolymers, improves the polymeric coating flow properties. The surfactant in the polymeric former coating is ethoxylated acetylenic diol or Surfynol 465 or other surfactants, such as Tween 20; etc. The water-soluble discrete coagulant particles are selected from a group comprising sodium chloride, potassium chloride, calcium nitrate, calcium chloride and aluminium sulphate. The sizes of water-soluble discrete coagulant particles range from about 50 microns to about 2000 microns.

The formers with this polymeric coagulant coating with embedded discrete coagulant particles are then dipped in an aqueous latex emulsion. The coagulant incorporated in the polymeric coagulant coating instantly destabilizes the latex emulsion in close proximity with the coated former surface, thereby forming a latex film layer. The water-soluble discrete coagulant particles also have the destabilizing property, and the latex emulsion also forms a latex film layer surrounding the particles. Thus, the latex layer completely covers the former surface, and the embedded water-soluble discrete coagulant particles are completely surrounded by the latex layer. Depending on the size and shape of these embedded particles, the latex layer may be re-entrant, meaning that stripping of the latex layer will require the plucking of the particle from the polymeric coagulant coating or expansion of the latex layer. The latex layer replicates the size and shape of the discrete coagulant particles embedded in the polymeric coagulant coating, maintaining the exact distribution of texture placed during the embedding step. The former, together with the latex layer, is subjected to a curing cycle during which the latex film cross-links and vulcanizes.

The latex composition used to create the geometrically textured glove can be made from natural or synthetic rubber and nitrile compositions. These aqueous latex compositions are well-known in the art and include standard compounding admixtures, such as sulfur, zinc oxide, organic accelerators, stabilizers, waxes, anti-aging substances, viscosity regulators, fillers, and pigments.

After the vulcanization process is complete, in one embodiment, the glove can be stripped and turned inside out. This can be a surgical or examination single layer glove. The glove strips easily from the former, since the water-soluble, discrete, coagulant particles that define the size, shape and distribution of texture are weakly held as compared to the bond between the vulcanized latex layer and the water-soluble, discrete coagulant particle. When the glove is turned out, the water-soluble, discrete, coagulant particles are now on the external surface of the glove. The external surface of the glove is washed in water, preferably hot water, to dissolve away the water-soluble, discrete, coagulant particles, leaving behind a texture with impressions that exactly replicate the size, shape and distribution of the water-soluble, discrete, coagulant particles initially placed on the polymeric former coating. If partially water-soluble or water-insoluble, discrete, coagulant particles are used, a solvent wash is needed to dissolve the discrete coagulant particles and to expose the impressions of glove external surface texture. The sodium chloride crystals have angular surfaces, and these are exactly replicated, providing a void in the texture that has a larger surface area or a larger pore volume than a circular pore formed by air-blown foam. Further, the pore opening at the external surface may be smaller than that in the interior due to the re-entrant nature of the replication process, a feature that is not possible when textured formers are used. Therefore, the suction cups of the texture formed have a large capacity to extract water or oil present on a wet or oily surface being gripped, thereby eliminating the water or oil boundary layer. A larger surface area of latex comes in contact with the surface being gripped, due to the re-entrant nature of the pores, providing increased gripping action. If the geometrical texture is designed such that the water-soluble, discrete, coagulant particles touch each other, the texture has pores that interconnect with each other, providing a channeling effect of boundary layer water or oil present in the boundary layer of a gripped surface.

After the vulcanization process is complete, in a second embodiment, the glove can be dipped in a coagulant solution and re-dipped in latex to form a second latex layer. The second latex layer can be a foamed latex layer. When the glove is turned inside out, the foamed surface contacts the skin and has the capacity to absorb perspiration and provide a less clammy feel. The external surface with water-soluble discrete particles is washed in a manner similar to the first embodiment revealing the glove geometrical texture.

After the vulcanization process is complete, in a third embodiment, the glove can be dipped in an adhesive coating and cotton or rayon fibers can be air-sprayed or electrostatically applied to produce a flocked fibrous coating. When the glove is turned inside out, the adhesive-coated rayon or cotton flock contacts the skin and provides moisture absorption properties. The fiber flock also results in soft skin contact, providing a comfortable, less clammy, glove feel. The external surface of the glove is washed in a similar manner as the first embodiment to reveal the glove geometrical texture.

After the vulcanization process is complete, in a fourth embodiment, the glove can be stripped and turned inside out and washed as disclosed in the first embodiment to produce a geometrically textured liner shell. A former is taken, and a knitted glove liner is slipped onto it. The knitted liner can be made from cotton, rayon, nylon, cut-resistant fibers, including Kevlar™ aramid fibers, Spectra™ polyethylene fibers, or braided steel fibers with a polyester sheath. An adhesive layer is applied to the knitted glove liner. The geometrically textured liner shell is slipped over the adhesive-coated knitted liner on the former and subjected to a curing cycle, which hardens the adhesive to form a flexible interface between the geometrically textured liner shell and the knitted glove liner. This construction results in a supported geometrically textured glove that has excellent gripping properties, together with cut resistance.

The key features of the latex gloves with geometrically defined, surface texture providing enhanced grip include, in combination, the features set forth below:

a glove surface which has geometrically textured features comprising a regular or irregular array of indentations or impressions;

the textured features having sizes, shapes and distribution of features selectable and precisely applied on the glove surface;

the textured features of indentations and or impressions having well-defined sharp edges;

the textured features of indentations and or impressions having re-entrant surfaces;

the textured features of indentations and or impressions having interior surface areas greater than a spherical void;

the glove external surface textured features of indentations and or impressions having interior volumes sufficient to suck and retain boundary layer oil or water present on a surface being gripped; and the glove textured surface free from voids, tears and defects formed during stripping from a glove former.

The key features of the process for producing a latex glove with geometrically defined surface texture providing enhanced grip include, in combination, the process steps set forth below:

formulating a polymeric coagulant coating comprising water-soluble polymer selected from PVP, PVA, PAA, PAC, and/or a copolymer or derivative of PVP, PVA, PAA or PAC, a coagulant selected from calcium nitrate and calcium chloride, polyglycol, and a surfactant;

applying the polymeric coagulant coating to a former used for dipping gloves in an aqueous latex emulsion;

drying the polymeric coagulant coating on glove former until the coating is tacky;

applying water-soluble, partially water-soluble, or water-insoluble discrete coagulant particles to the tacky polymeric coagulant coating on the glove former;

drying the polymeric coagulant coating with embedded discrete particles on the glove former;

in-line or sequential dipping of polymeric, coagulant-coated, discrete particle-embedded, glove former in an aqueous latex emulsion;

destabilizing and coagulating the latex emulsion on the polymeric coagulant coating and on discrete coagulant particles embedded in the polymeric coagulant coating, forming a latex film that surrounds and incorporates discrete coagulant particles in the latex film;

subjecting the former with the latex film to a cure cycle to vulcanize latex;

in first embodiment, stripping the surgical or examination glove of vulcanized latex film from the former, inverting it, and washing it to dissolve the discrete coagulant particles in water or appropriate solvents, thereby exposing a geometric texture on the external surface of the glove;

in a second embodiment, applying a second layer of foamed latex, curing the foamed latex layer, stripping the industrial glove from the former, inverting it inside out and washing with water or appropriate solvents to dissolve the discrete coagulant particles, thereby exposing a geometric texture on the external surface of the glove;

in a third embodiment, applying an adhesive layer, followed by air spray or electrostatic spray of cotton or rayon flock, curing the adhesive layer, stripping the industrial glove from the former, inverting it inside out to produce a moisture-wicking glove skin contact interior surface, and washing with water or appropriate solvents to dissolve the discrete coagulant particles, exposing geometric texture on the external surface of the glove; and in a fourth embodiment, producing a vulcanized latex glove shell on the former as detailed in step 8 by applying a non-tacky adhesive layer of polyurethane to the vulcanized latex glove shell, slipping a knitted liner over the adhesive-coated, vulcanized latex shell, melting the polyurethane adhesive by application of heat to bond the vulcanized latex glove shell with the knitted liner, stripping the supported glove from the former, inverting it to expose the discrete coagulant particles, and washing the inverted glove with water or appropriate solvents to dissolve discrete coagulant particles, thereby exposing the geometrically textured glove surface.

Thus, in disclosure of the principle herein, a method of producing by conventional dipping methods geometrically textured synthetic or natural latex articles, in particular, articles produced for industrial, household and medical glove applications, is provided.

DETAILED DESCRIPTION OF THE INVENTION

Figure 1:
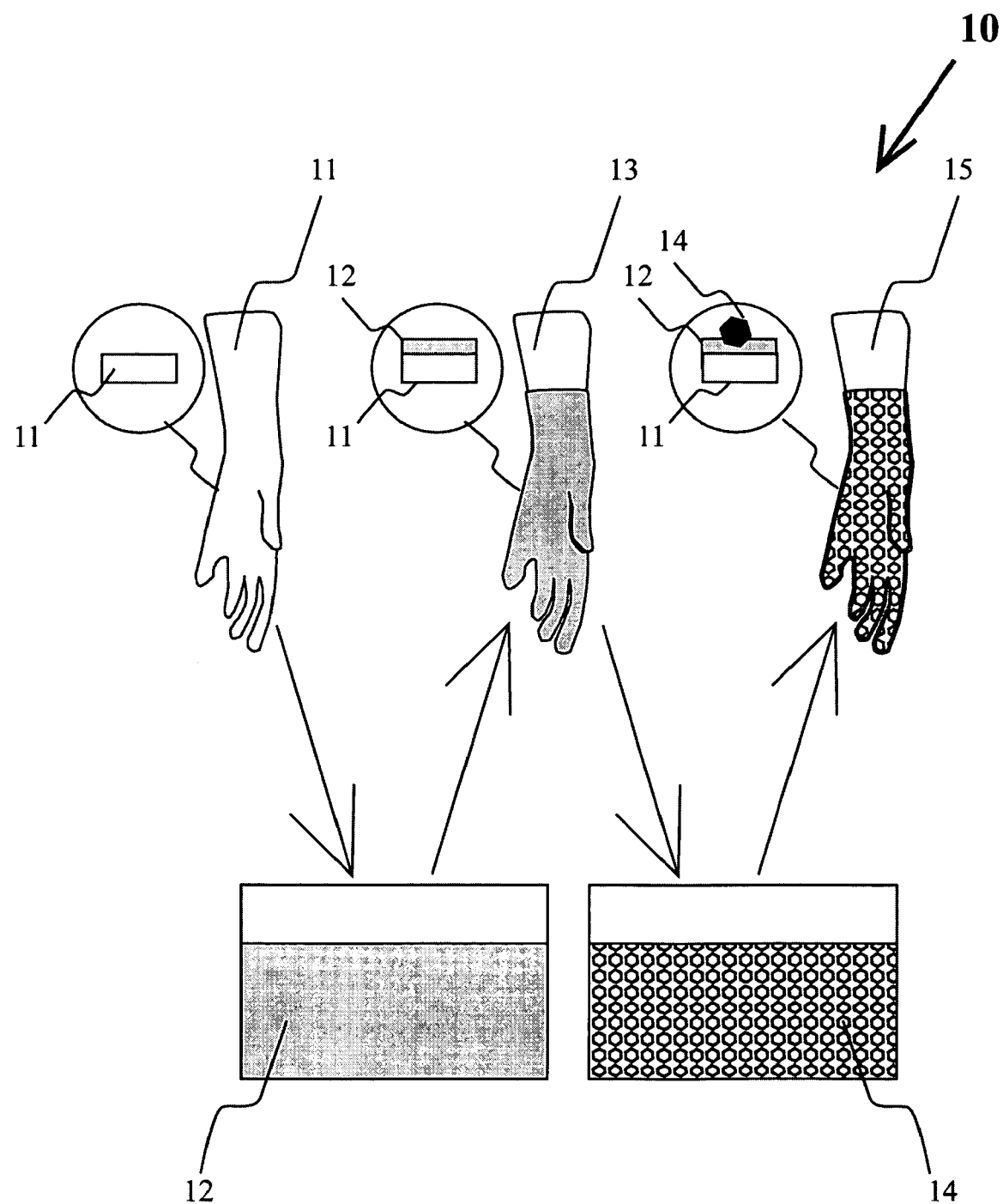
FIG. 1 is a diagrammatic representation of an in-line processing of a glove former by first dipping in a polymeric coagulant coating composition, drying the former external surface coating until the coating is tacky, applying discrete coagulant particles to the tacky coating, and drying the polymeric coagulant coating with embedded particles.

Latex gloves with geometrically defined surface structure provide the ability to vary the grip according to the size, shape and distribution of discrete coagulant particles that are attached to the polymeric coagulant coating applied to the smooth former used for dipping the glove. The process can use water-soluble, partially water-soluble, or water-insoluble discrete, coagulant particles. These discrete coagulant particles are embedded by a dry powder coating process onto a tacky, water-soluble, polymeric, coagulant coating or film built up on the smooth former. When the surface texture is applied selectively to specific areas of the glove external surface, the polymeric coagulant coating holds discrete coagulant particles in the palm and finger areas before the former with embedded discrete coagulant particles is dipped into the synthetic or natural aqueous latex emulsion to form the latex film. The ability to obtain precisely shaped and distributed concave indentations or suction cup shapes on the external gripping surface of a dipped latex film arises from the embedded discrete coagulant particles held in precise locations by the water-soluble polymeric coagulant coating or film. After the latex film of the glove is cured, the glove is inverted to expose the discrete coagulant particles that are dissolved by a water wash, preferably a hot water wash, or by an appropriate solvent wash.

Generally stated, the present invention provides a method of achieving precisely defined suction cups or indentations with preferably angular shapes with controlled size and distribution on the external grip surface of the geometrically textured glove using an in-line manufacturing process that is akin to most commercial glove manufacturing processes. The process uses a standard smooth glove former and discrete coagulant particles are attached to its surface using a water-soluble polymeric coagulant coating applied first to the former with a thickness range of about 5 to 50 µ. The impressions are created in the latex layer due to the coagulating action of the polymeric coagulant coating and the embedded discrete coagulant particles. When the latex layer is cured, stripped, and inverted, the outer layer of the glove with exposed discrete coagulant particles is washed to dissolve the embedded particles and expose the surface texture of the textured glove. The former is readily washed, since the polymeric coagulant coating dissolves in water, and the former is ready for the next processing cycle with no damage. As a consequence of the geometrical texture created on the glove external surface with very high reliability and precision, the glove provides improved ability to hold tools and instruments under dry, wet and oily environments. The degree of traction or gripping power provided by the textured external surface of the glove can be selected in a controlled manner by selecting the particle size of the discrete, coagulant particles that are used. Fine, discrete coagulant particles in the size range of about 50 to 200 µ result in smoother traction as compared to coarse, discrete coagulant particles in the size range of about 150 to 2,000 µ.

The water-soluble, polymeric, coagulant coating solution uses a polymer selected from the group comprising PVP, PVA, PAA, PAC, and/or a copolymer or derivative of PVP, PVA, PAA or PAC. Examples of such copolymers are 1) a copolymer of 1-vinyl-2-pyrrolidone and 1-methyl-3-vinyl-imidazolium-methylsulfate and 2) a copolymer of vinylcaprolactam/vinyl pyrrolidone/dimethylaminoethyl methacrylate. Examples of polyacrylic acids include a range of water-soluble acrylic homopolymers and/or methacrylic acid homopolymers. PVP or PVP copolymer and PAC are commonly used as the primary ingredients in hairstyling products. With the same principle, the polymer or its copolymer will hold the water-soluble, partially water-soluble or water-insoluble discrete coagulant particles in place on the palm and finger areas of the former before the former is dipped into a synthetic or natural aqueous latex emulsion. The amounts of water-soluble polymer incorporated into the polymeric coagulant coating can be varied in the range of 0.01% to 10% dry weights. Ideally, the level should be in the range of 0.5% to 1.5% to give enough tackiness to hold discrete coagulant particles on the former surface.

The water-soluble, discrete, coagulant particles are selected from a group comprising all kinds of dry salts, which exhibit latex emulsion coagulating action and which are applied through a dry powder coating process. Examples of salts suitable for discrete, coagulant particles include sodium chloride, potassium chloride, calcium nitrate, calcium chloride, and aluminium sulphate.

Even though it is preferable to use water-soluble, discrete, coagulant particles embedded in the polymeric coagulant coating on the former, it is possible to use water-insoluble, discrete, coagulant particles, such as calcium carbonate or sodium bicarbonate, applied through the dry powder coating process and then washed off after latex vulcanization, using an acid wash, instead of a water wash. The dry powder coating application of discrete coagulant particles can be carried out using standard techniques commonly used in the industries, such as a sprinkling system, a pressurized spray, and atomizing and fluidized air beds.

Referring to FIG. 1, there is shown generally at 10 a diagrammatic representation of an in-line processing of a glove former 11 by first dipping in a polymeric coagulant coating composition 12, drying the former external surface coating until the coating is tacky as shown at 13, applying water-soluble, discrete, coagulant particles 14 to the tacky coating, and drying the polymeric coagulant coating with embedded particles as shown at 15. The details of the surfaces at each process step are shown in a circular magnified view. In the first step, only the former 11 is present. After dipping in the polymeric coagulant coating solution and drying, a tacky coating layer is formed as shown in the magnified view of step 2, which shows the former 11 with the tacky coating 12. Now in step 3, the discrete coagulant particles are applied to the tacky polymeric coagulant coating as shown in the magnified view. The polymeric coagulant coating 12 now has an embedded discrete coagulant particle 14. In this illustration the thumb, fingers, and palm region up to the cuff region are dipped in the polymeric, coagulant coating solution. However, the tacky coating can be applied only to selected regions of the glove.

Figure 2:
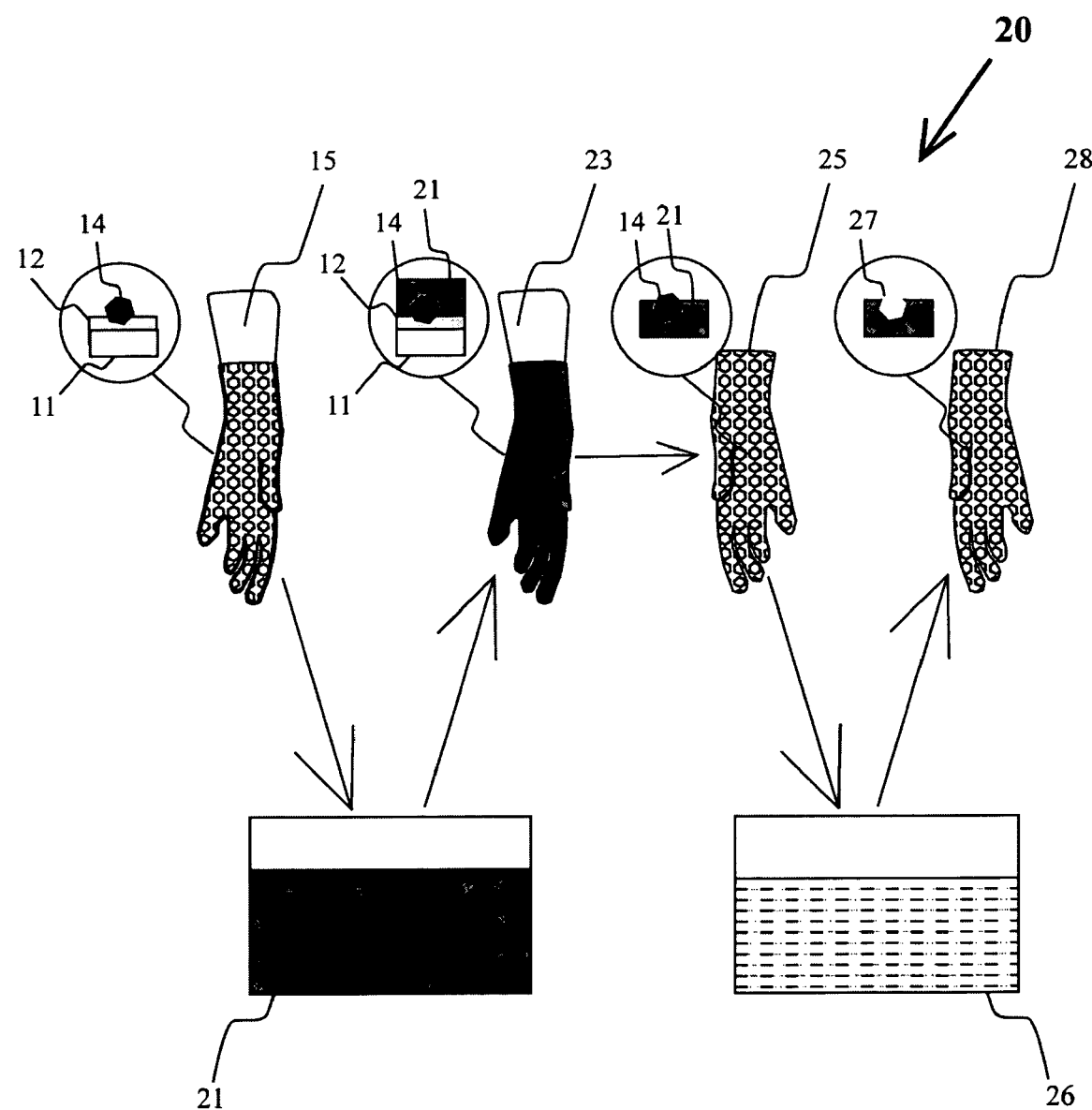
FIG. 2 is a diagrammatic representation of an in-line processing line in which 1) a dipping station, in which a former coated with a polymeric coagulant coating with embedded water-soluble discrete coagulant particles is dipped in an aqueous latex emulsion, forming a film of coagulated latex that surrounds discrete coagulant particles; 2) a heating station vulcanizing latex film; 3) a stripping station; 4) a glove inversion station; and 5) a water wash station to dissolve discrete coagulant particles are shown.

Referring to FIG. 2, there is shown generally at 20 a diagrammatic representation of an in-line processing line in which a dipping station, in which a former 15, which is coated with a polymeric coagulant coating with embedded water-soluble discrete coagulant particles 14, is dipped in an aqueous latex emulsion 21, forming a film of coagulated latex that surrounds the water-soluble, discrete, coagulant particles 14. A heating station (not shown) vulcanizes the latex film. A stripping station 25 is shown, where the glove is stripped from the former and is inverted with the discrete coagulant particles 14 on the exterior surface as shown in the magnified view. A water wash station 26 is provided to dissolve discrete coagulant particles 14. The dissolved particles leave a re-entrant angular impression as shown at 27 in the magnified view.

Figure 3A:
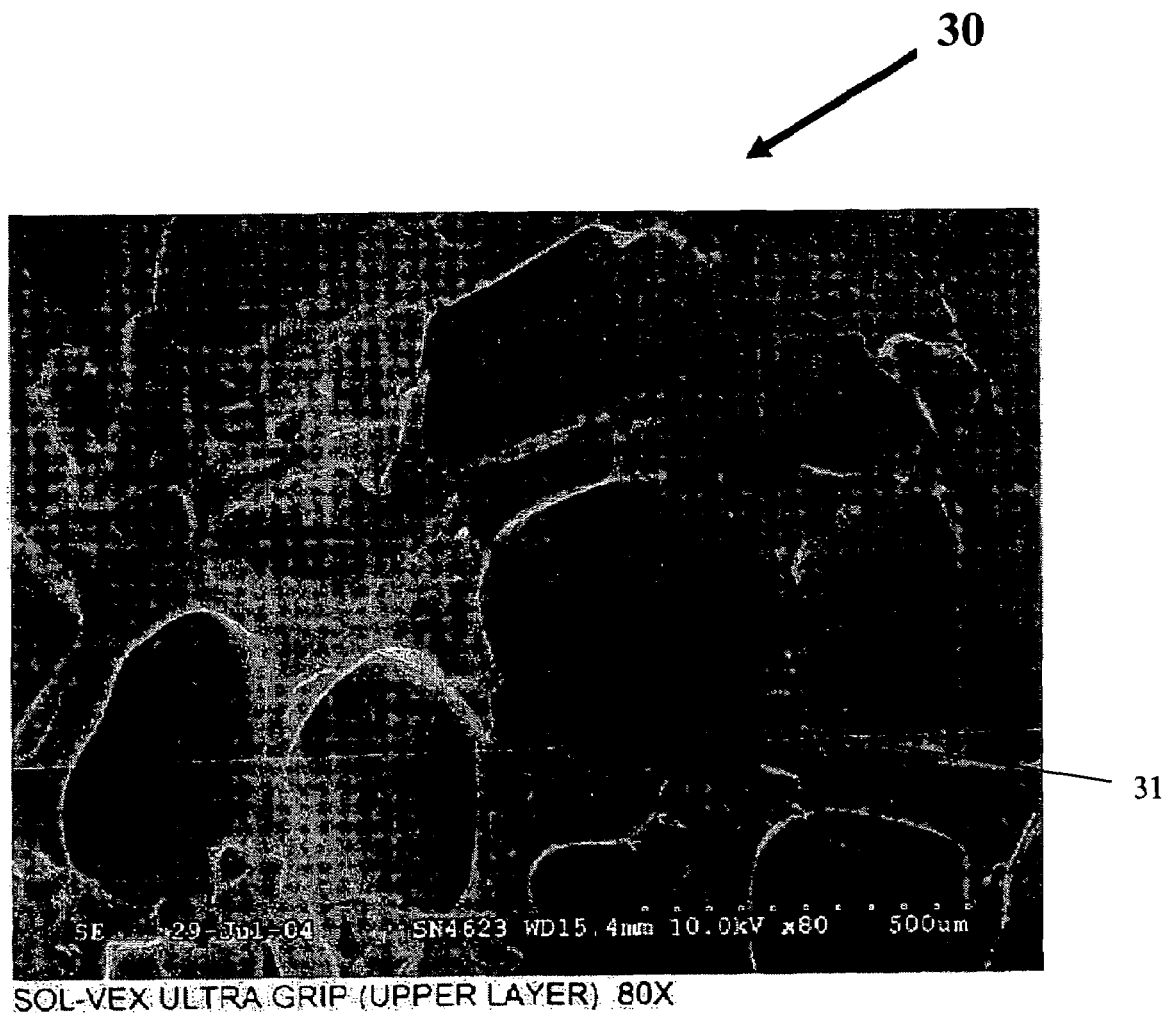
FIG. 3A is a scanning electron micrograph of the gripping external surface of the glove at 80× showing precise replication of the angular features of the embedded water-soluble discrete coagulant particles.

Referring to FIG. 3A, there is shown at 30 a scanning electron micrograph of the gripping external surface of the glove at 80× showing precise replication of angular features of the embedded, water-soluble, discrete, coagulant particles at 31. The discrete coagulant particles of sodium chloride have a size range of about 300-1630 µ as indicated in Example 4 below.

Figure 3B:
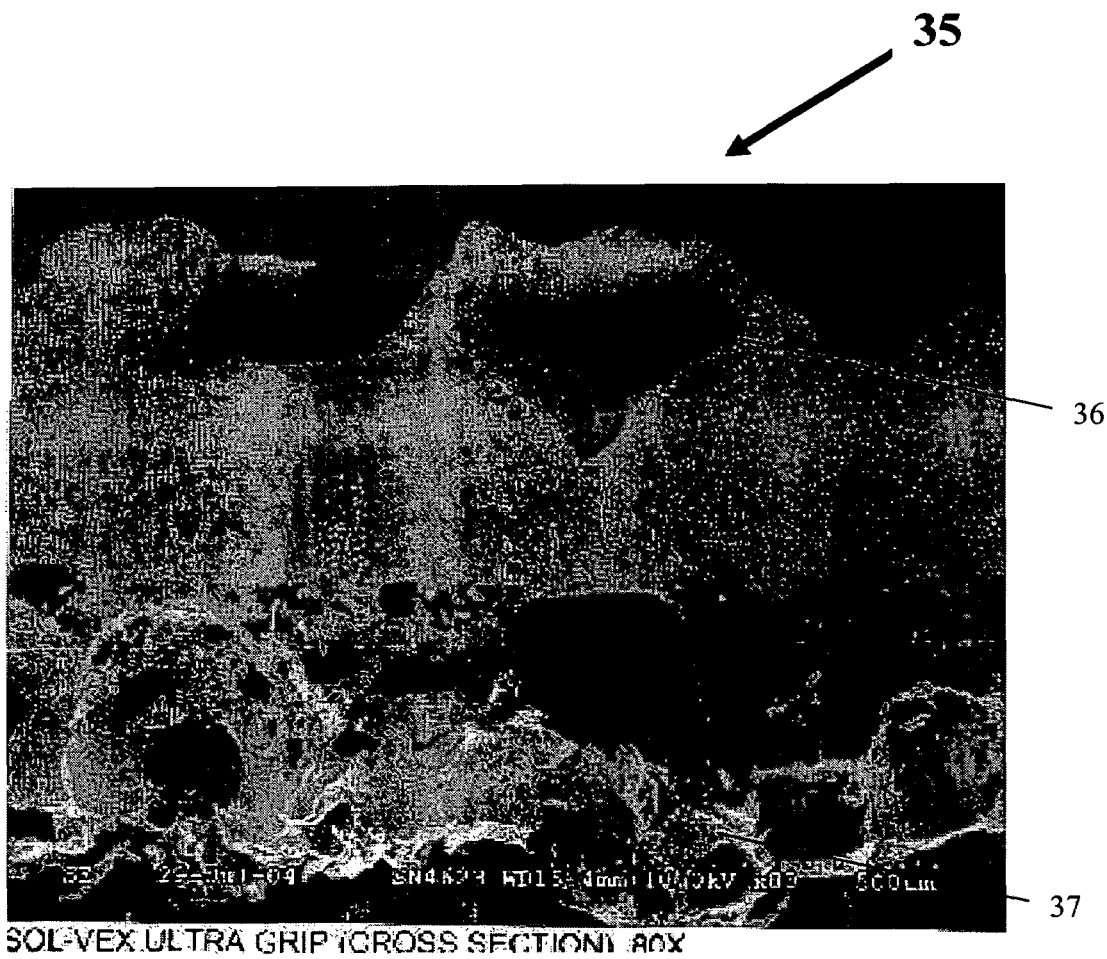
FIG. 3B is a scanning electron micrograph of the cross section of the gripping external surface of the glove at 80× showing precise replication of the angular features of the embedded, water-soluble, discrete, coagulant particles.

Referring to FIG. 3B, there is shown at 35 a scanning electron micrograph of the cross section of the gripping external surface of the glove at 80× showing precise replication of the angular features of the embedded, water-soluble, discrete, coagulant particles and the presence of a re-entrant impression at 36. The discrete coagulant particles of sodium chloride have a size range of about 300-1630 µ as indicated in Example 4 below. The foam layer is clearly seen in the micrograph under the latex layer at 37 and is discussed in Example 9 below.

Figure 4A:
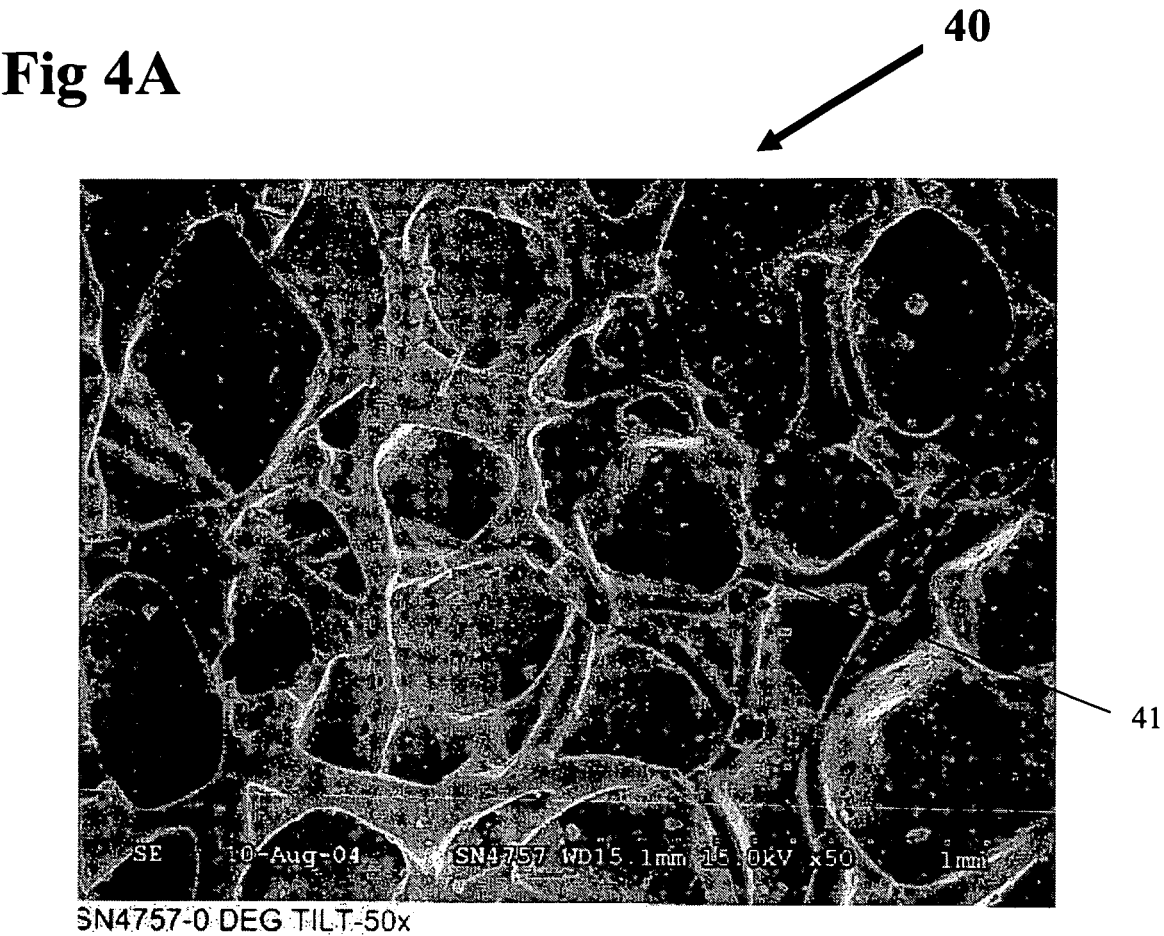
FIG. 4A is a scanning electron micrograph of the gripping external surface of the glove at 50× showing precise replication of the angular features of the embedded, discrete, coagulant particles.

Referring to FIG. 4A, there is shown at 40 a scanning electron micrograph of the gripping external surface of the glove at 80× showing precise replication of angular features of the embedded, water-soluble, discrete, coagulant particles at 41. The discrete coagulant particles of sodium chloride have a smaller size range of about 470-700 µ as indicated in Example 6 below.

Figure 4B:
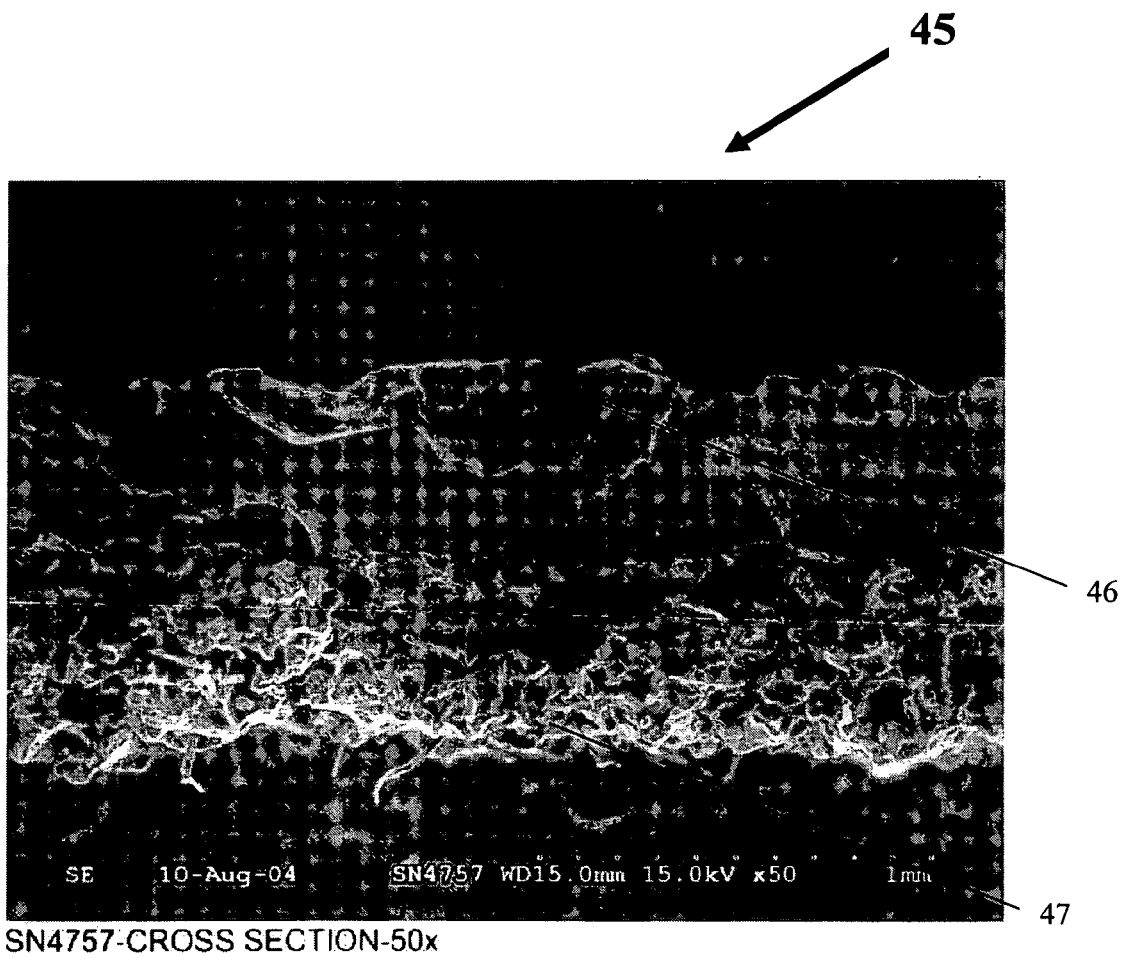
FIG. 4B is a scanning electron micrograph of the cross section of the gripping external surface of the glove at 50× showing precise replication of the angular features of the embedded, discrete, coagulant particles.

Referring to FIG. 4B, there is shown at 45 a scanning electron micrograph of the cross section of the gripping external surface of the glove at 50× showing precise replication of the angular features of the embedded, water-soluble, discrete, coagulant particles and the presence of a re-entrant impression at 46. The discrete coagulant particles of sodium chloride have a smaller size range of about 470-700 µ as indicated in Example 6 below. The flock is clearly seen in the micrograph under the latex layer at 47 and is discussed in Example 9 below.

EXAMPLES

The following examples serve to illustrate the present invention and are not intended to limit its scope in any way.

Example 1 (Comparative Example)

A clear coagulant solution was prepared having the following composition:

| Constituent | Dry weight: |
|---|---|
| Calcium Nitrate | 40.00% |
| Polyethylene glycol 3350 | 0.50% |
| Surfynol 465 | 0.15% |
| Water | balance to 100% total weight. |

A heated porcelain former was dipped into the above polymeric coagulant solution heated to 50-60° C. and was dried for 2 min at 40° C. Using a standard air-pressurized powder sprayer, fine sodium chloride discrete coagulant particles are sprayed onto the palm and finger regions of the dry coagulant surface of the former.

There was poor adhesion of sodium chloride discrete coagulant particles to the palm and finger areas of the former, resulting in patchy spots of salt deposits. There is a high likeliness of pinholes and thin patches as defects in gloves produced using this method.

The former was then dipped into the following standard nitrile industrial glove latex composition followed by leaching for 2 min at 40° C.

| Composition | Dry weight % |
|---|---|
| Nitrile latex | 100 |
| Potassium Hydroxide solution | 65% |
| Sodium lauryl sulphate | 0.72 |
| Zinc Oxide | 3.25 |
| Sulphur | 0.5 |
| Dithiocarbamate accelerator | 0.25 |
| Bactericide | 0.25 |

-continued

| Composition | Dry weight % |
|---|---|
| De-foamer | 0.6 |
| Color Pigment | 0.3 |
| Titanium dioxide | 0.5 |

The glove was then cured in the oven for 35 min at 100° C. The resultant glove was then stripped from the former. The glove had poor texture appearance at the palm and finger areas with some smooth and rough patches throughout the palm and finger areas.

Example 2

Another coagulant was prepared according to the following composition:

| Composition | Dry weight: |
|---|---|
| Calcium Nitrate | 40.00% |
| Polyethylene glycol 3350 | 1% |
| PVP copolymer | 0.50% |
| Surfynol 465 | 0.15% |
| Water | balance to 100% total weight. |

Similar glove dipping steps were carried out as in Example 1. The sodium chloride discrete coagulant particles had good adhesion to the dry coagulant on the palm and finger surface areas of the former. As the glove was stripped from the former, the glove was turned inside out, and it had a uniform rough texture at the palm and finger areas, although some salt deposit had penetrated through the dried polymeric coagulant coating layer glove causing many tiny pinholes.

Example 3

Another coagulant was prepared according to the following composition:

| Composition | Dry weight: |
|---|---|
| Calcium Nitrate | 40.00% |
| Polyethylene glycol 3350 | 1% |
| PVP copolymer | 1.00% |
| Surfynol 465 | 0.15% |
| Water | balance to 100% total weight. |

Similar glove dipping steps were carried out as in Examples 1 and 2. A similar observation as in Example 2 was recorded, except that the number of pinholes on gloves produced using this coagulant was reduced drastically as compared to the previous examples.

Example 4

Another coagulant was prepared according to the following composition:

| Composition | Dry weight: |
|---|---|
| Calcium Nitrate | 40.00% |
| Polyethylene glycol 3350 | 1% |
| PVP copolymer | 1.50% |
| Surfynol 465 | 0.15% |
| Water | balance to 100% total weight. |

After the heated former was dipped into the above coagulant, sodium chloride (300-1630 µ) discrete coagulant particles were manually sprinkled uniformly around the palm and finger areas of the former. The tacky coagulant was able to hold the deposited salts evenly until the former was dipped into the nitrile latex composition as in Example 1. A similar observation as in Examples 2 and 3 was recorded, except that there were a few gloves with pinholes produced using this coagulant, indicating that, if the PVP copolymer film was thicker and the discrete coagulant particles were distributed evenly, the medium to coarse sodium chloride discrete coagulant particles could be embedded into it with minimum impact to the first layer of the nitrile laminate.

The above glove texture appearance at the palm and finger areas was captured on a scanning electron microscope (SEM) at 80× magnification across the upper surface and cross-section as in FIGS. 3A and 3B. The suction cup indentations that formed on the surface from the shapes of the embedded salts after the glove was washed are obvious from the SEM photographs.

Example 5

The above experiment was repeated by replacing PVP with PVA as in Example 4. Similar phenomena were observed as in Example 4 using PVA, indicating that PVA can be used to replace PVP.

Example 6

A similar experiment as in Example 4 was repeated by dry spray coating much finer sodium chloride (470-700 µ) discrete coagulant particles using a fluidized air bed unit. The deposition of discrete coagulant particles on the former was more consistent than manual or air powder spraying, and no pinholes were observed. The stripped glove was examined with an SEM at 50× magnification across the upper surface and cross-section as shown in FIGS. 4A and 4B.

Example 7

Another experiment was repeated as in Example 6 until after the dry impregnation of salts onto the water-soluble, polymer coagulant-coated former, after which the former was then dipped for a shorter dwell time, approximately 10 sec in the first latex dip as a first laminate, followed with another longer dwell of 40 sec for the second dip as a second laminate. The former was then dipped in 10% calcium nitrate solution before being dipped into a foamed latex composition. The glove was then cured in the oven for 35 min at 100° C. The glove was then stripped and turned inside out. It was then watered off-line to remove excess salts and surfactants from the glove. The washed glove was then dried in the tumbler drier for 1 hr at 55° C. The three-layer laminate gloves that were produced using this method had a low likeliness of pinhole defects.

The three-layer laminate glove had good, comfortable donning, and dry, wet and oil grip features for industrial gloves. When six gloves were dipped using similar steps and were tested for dry, wet, and oil grips using standard Ansell test method TM 126, the readings were as follows:

| | Measurement/oz | | |
|---|---|---|---|
| Test specimen | Dry Grip | Wet Grip | Oil Grip |
| 1 | 96 | 40 | 44 |
| 2 | 104 | 40 | 44 |
| 3 | 112 | 48 | 44 |
| 4 | 96 | 40 | 44 |
| 5 | 104 | 44 | 40 |
| 6 | 96 | 40 | 40 |
| Average | 101 | 42 | 43 |

The dry and oil grips (as determined using standard Ansell test method TM 126) were benchmarked against typical, standard Ansell Solvex Industrial gloves as follows:

| | Measurement/oz | |
|---|---|---|
| Test specimens: | Average Dry Grip | Average Oil Grip |
| Commercial Solvex 37-145 | 61 | 22 |
| Commercial Solvex 37-165 | 57 | 17 |
| Commercial Solvex 37-175 | 50 | 24 |
| Commercial Solvex 37-185 | 45 | 29 |
| Commercial Solvex 37-500 | 80 | 16 |
| Commercial Solvex 37-510 | 39 | 12 |
| Commercial Solvex 37-646 | 56 | 16 |
| Commercial Solvex 37-650 | 51 | 15 |
| Commercial Solvex 37-900 | 26 | 10 |
| Experimental gloves | 101 | 43 |

Clearly, the experimental gloves produced with geometrically defined surface texture provide enhanced dry, wet, and oil grip features as compared to any of the commercial gloves thus far produced.

Example 8

Another experiment was repeated except that, after the second nitrile latex laminate, the former was then dipped into a mild chlorine solution. The glove is cured, stripped, off-line washed and dried as in Example 7. The two-layer laminated gloves produced from this method had a low likeliness of pinhole defects. The two-layer laminate glove had good donning and dry, wet, and oil grip features.

Example 9

Another experiment was repeated except that, after the second nitrile latex laminate, the former was dipped in an adhesive latex. A cotton or rayon flock was applied to the adhesive layer by air-blowing or an electrostatic method. The glove was then stripped inside out, was off-line washed, and then dried as in the previous examples. The three-laminate glove produced with this method had good donning flock and dry, wet, and oil grip features. The use of discrete, coagulant, salt particles to impregnate the water-soluble polymer coagulant surface is depicted in the micrographs of FIGS. 3B and 4B. The flock is clearly seen in the micrograph under the latex layer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of making a latex article with a geometrically defined surface texture, which method comprises:
    dipping a smooth former into a polymeric coagulant composition comprising a water-soluble polymer, a polyglycol, a surfactant, and a coagulating salt;
    drying the polymeric coagulant composition to form a tacky, polymeric coagulant coating;
    applying discrete coagulant particles to the tacky, polymeric coagulant coating;
    dipping the former into a coagulatable aqueous latex emulsion, and destabilizing the latex emulsion in close proximity to the former, thereby forming a coagulated first latex layer that covers the discrete coagulant particles and external surface of the former;
    heating the former to form a first cured latex layer by vulcanization or curing;
    stripping and inverting the first cured latex layer to expose the discrete coagulant particles; and
    leaching or dissolving the discrete coagulant particles in water or an appropriate solvent;
    whereupon the latex article with the geometrically defined surface texture is obtained.

2. The method of claim 1, wherein the polymeric coagulant coating has a thickness in the range of about 5 to 50 microns.

3. The method of claim 1, wherein the water-soluble polymer is poly N-vinyl-2-pyrrolidone (PVP), polyvinyl alcohol (PVA), polyacrylic acid (PAA), polyacrylamide (PAC), copolymers thereof, or derivatives thereof.

4. The method of claim 3, wherein the water-soluble polymer is present in the polymeric coagulant coating in an amount ranging from about 0.01% to about 10.0%, based on dry weight.

5. The method of claim 4, wherein the water-soluble polymer is present in the polymeric coagulant coating in an amount ranging from about 0.5% to about 1.5%, based on dry weight.

6. The method of claim 3, wherein the PAA is an acrylic homopolymer.

7. The method of claim 6, wherein the acrylic homopolymer is methacrylic acid homopolymer.

8. The method of claim 3, wherein the copolymer is a copolymer of PVP and 1-methyl-3-vinyl-imidazolium-methylsulfate.

9. The method of claim 3, wherein the copolymer is vinylcaprolactam/vinyl pyrrolidone/dimethylaminoethyl methacrylate.

10. The method of claim 1, wherein the polyglycol is polyethylene glycol.

11. The method of claim 1, wherein the polyglycol is polyethylene oxide/polypropylene oxide copolymers.

12. The method of claim 1, wherein the surfactant is an ethoxylated acetylenic diol.

13. The method of claim 1, wherein the coagulating salt is calcium nitrate or calcium chloride.

14. The method of claim 1, wherein the discrete coagulant particles range in size from about 5 to 1,800 microns.

15. The method of claim 1, wherein the discrete coagulant particles are water-soluble and selected from the group consisting of sodium chloride, potassium chloride, calcium nitrate, calcium chloride, aluminum chloride, and aluminum sulfate.

16. The method of claim 1, wherein the discrete coagulant particles are partially water soluble or water-insoluble and comprise one or more of calcium carbonate, magnesium carbonate, sodium carbonate, and sodium bicarbonate.

17. The method of claim 1, wherein the coagulatable aqueous latex emulsion is comprises carboxylated acrylonitrile butadiene, non-carboxylated acrylonitrile butadiene, butyl latex, polychloroprene, natural rubber, synthetic polyisoprene, or polyurethane.

18. The method of claim 17, wherein the coagulatable aqueous latex emulsion further comprises a curative.

19. The method of claim 1, further comprising:
    dipping the former into the aqueous latex emulsion for a second time after the step of heating the former to form the first cured latex layer by vulcanization or curing;
    forming a second cured latex layer by vulcanizing or curing; and
    wherein the stripping and inverting step includes stripping and inverting the second cured latex layer in combination with the first cured latex layer.

20. The method of claim 1, further comprising:
    dipping the former with the first cured latex layer into a foamed aqueous latex emulsion after the step of heating the former to form the first cured latex layer by vulcanization or curing;
    forming a foamed cured latex layer by vulcanizing or curing; and
    wherein the stripping and inverting step includes stripping and inverting the foamed cured latex layer in combination with the first cured latex layer.

21. The method of claim 1, further comprising:
    applying an adhesive layer to the first cured latex layer after the step of heating the former to form the first cured latex layer by vulcanization or curing;
    air blowing or electro-statically blowing cotton or rayon flock over the adhesive layer, thereby forming a flocked layer;
    curing the adhesive layer;
    wherein the stripping and inverting step includes stripping and inverting the flocked layer in combination with the first cured latex layer.

22. The method of claim 1, further comprising:
    applying a non-tacky polyurethane adhesive layer to the first cured latex layer at room temperature after the step of heating the former to form the first cured latex layer by vulcanization or curing;

applying a knitted liner comprising cotton, an aramid fiber, a polyethylene fiber, a steel wire, or combinations thereof over the non-tacky polyurethane adhesive layer;

heating the former to melt the non-tacky polyurethane adhesive layer, thereby forming a flexible bond between the first cured latex layer and the knitted liner; and wherein the stripping and inverting step includes stripping and inverting the knitted liner in combination with the first latex layer.

23. The method of claim 1, wherein the step of applying discrete coagulant particles to the tacky, polymeric coating is done according to a design that includes details of size, shape, and distribution of the particles on the former.

* * * * *